United States Patent  [10] Patent No.: US 6,858,054 B2
Page  [45] Date of Patent: Feb. 22, 2005

(54) FAN ASSEMBLY AND STORAGE CHAMBER UTILIZING A FAN ASSEMBLY

(76) Inventor: George Page, 421 Lower Broughton Road, The Cliff, Salford, Manchester M7 2EZ (GB)

( * ) Notice: Subject to any disclaimer, the term of this patent is extended or adjusted under 35 U.S.C. 154(b) by 87 days.

(21) Appl. No.: 10/415,855
(22) PCT Filed: Feb. 7, 2001
(86) PCT No.: PCT/GB01/00467
  § 371 (c)(1),
  (2), (4) Date: May 2, 2003
(87) PCT Pub. No.: WO02/36904
  PCT Pub. Date: May 10, 2002

(65) Prior Publication Data
  US 2004/0074530 A1 Apr. 22, 2004

(30) Foreign Application Priority Data
  Nov. 2, 2000 (GB) .............................. 0026805

(51) Int. Cl.[7] .................. B01D 50/00; B01D 59/00; E04H 15/14
(52) U.S. Cl. .................. 55/385.2; 135/93; 52/2.11
(58) Field of Search .................. 55/385.2; 135/93; 52/2.11, 2.23, 2.24

(56) References Cited

U.S. PATENT DOCUMENTS 4,991,363 A * 2/1991 Randmae ............... 52/2.11
6,119,408 A * 9/2000 Page ..................... 52/2.23

* cited by examiner

Primary Examiner—Robert A. Hopkins
(74) Attorney, Agent, or Firm—Andrus, Sceales, Starke & Sawall, LLP

(57) ABSTRACT

A fan assembly (14) for ventilating an essentially closed chamber such as an inflatable storage chamber for a motor vehicle comprises a base plate (17) for mounting over an opening through a wall (13) of the chamber, the base plate defining an aperture (21) therethrough and an electrically-driven fan (28) being arranged to draw air from a first plenum (31) upstream of the fan and drive the drawn air into the chamber. An air treatment unit (25) is disposed over an opening through the base plate between the chamber and the first plenum (31). A first filter (22) is disposed in an opening between the first plenum (31) and the external atmosphere (35). In this way, air driven into the chamber by the fan (28) will be a mixture of air drawn from the external atmosphere through the first filter (22) and air drawn from the chamber through the air treatment unit (25) into the first plenum (31), to be recirculated into the chamber.

14 Claims, 5 Drawing Sheets

FAN ASSEMBLY AND STORAGE CHAMBER UTILIZING A FAN ASSEMBLY

CROSS-REFERENCE TO RELATED APPLICATIONS

This application is the U.S. national stage application of International Application PCT/GB01/00467, filed 7 Feb. 2001, which international application was published on 10 May 2002 as International Publication WO 02/36904 in the English language. The International Application claims priority of Great Britain Patent Application No. 0026805.2 filed 2 Nov. 2000.

BACKGROUND OF THE INVENTION

This invention relates to a storage chamber in the form of an essentially closed space in conjunction with a fan assembly for ventilating that space.

A known form of inflatable storage chamber for articles such as vintage cars and motor-cycles or other delicate machinery such as aero-engines is described in EP-0859105-A and comprises a flexible plastics material cover sheet connected to a base sheet thereby to define an essentially closed space within which the article to be stored may be positioned. One or more low-power fans are arranged to direct air into the chamber defined by the two sheets so as to inflate the space and so form the storage chamber. In order to prevent condensation within the chamber, which could damage for example paintwork on a vintage car, it is also known to treat the air entering the chamber, for example with a vapour-phase corrosion inhibitor and also to ensure that the air in the chamber is slowly replaced by fresh air from the external atmosphere.

SUMMARY OF THE INVENTION

A problem with inflatable storage chambers as described above is that in the event the relative humidity of the external atmosphere is high, condensation can still occur inside the storage chamber, especially should the external temperature fall. At times, it may be better to recirculate the air within the chamber rather then introduce fresh air having a relatively high humidity, particularly if the humidity of the air inside the chamber is lower than that outside the chamber. It would be possible to arrange manually openable and closeable vents to allow control, but an aim of inflatable storage chambers as described in EP-0859105-A is that products may be stored for long periods without the need for any manual intervention, for example, should the climatic conditions change.

Fan units for the filtration of air are known for example from DE-29916321-U1, but this fan unit is intended as part of an ultra-clean room for use in pharmaceutical or biotechnical fields and is not really suitable for use with a storage chamber for a motor vehicle.

In view of the above it is a principal aim of the present invention to provide an inflatable storage chamber with a fan assembly, to enhance the storage conditions within the chamber. In particular, improved storage conditions can be achieved, with particular reference to reducing the likelihood of condensation within the chamber.

Accordingly, one aspect of the present invention provides a storage chamber comprising an essentially closed space defined by a base sheet, flexible plastics material cover the periphery of which is connected to the base sheet but which cover is at least partially releasable from the base sheet to give access to the space, and a fan assembly including an electrically-driven fan being mounted to an opening through the cover to drive air into the essentially closed space to inflate the chamber, characterised in that the fan assembly has a base plate defining an aperture therethrough and is adapted for mounting to said opening through the cover, and a first plenum chamber is formed on the upstream side of the fan whereby the fan draws air from the first plenum chamber and drives that air through the aperture in the base plate into said space, the fan assembly further including an air treatment unit disposed in or over a further opening through the base plate between said space and the first plenum chamber and a first filter disposed in or over an opening between the first plenum chamber and the external atmosphere, whereby the air driven into said space is a mixture of air drawn from the external atmosphere through the first filter and air drawn from said space through the air treatment unit into the first plenum chamber which latter air is recirculated into the space.

It will be appreciated that when the storage chamber of this invention is inflated and ventilated by operation of the fan assembly, some of the air already within the chamber is recirculated by the fan but during that recirculation is mixed with fresh air drawn in from the external atmosphere, through the first filter. In this way, the replacement of air within the chamber by filtered air from the external atmosphere is reduced. This will lead to a reduction in the wastage of any treatment agent which may be entrained in the air flow into the chamber. Moreover, the rate of change of the relative humidity of the air in the chamber can be significantly reduced, so in turn minimising the likelihood of damaging condensation on articles stored within the chamber.

Depending upon the kind of storage chamber and the products to be stored therein, the air treatment unit may take a number of different forms. For example, it could comprise a simple second filter, though perhaps of a different filtering capacity or pore size from those of the first filter. Alternatively the second filter could be of a different kind, such as an activated carbon filter.

The second filter may be provided within or sealed to the aperture in the base plate and may itself have an opening within which is mounted the fan. In the alternative, the fan may be mounted in an opening through a block of firm but resilient material, which resilient material is supported in or over the aperture through the base plate.

Another possibility for the air treatment unit is for it to include means to entrain a treatment liquid in the airflow from the closed space to the first plenum chamber. Such a treatment liquid could comprise a known form of a vapour-phase corrosion inhibitor to reduce the likelihood of corrosion of an article stored within the chamber. Another possibility is for the air treatment unit to include means to cool the airflow from the storage chamber to the first plenum chamber. Provided sufficient cooling of that airflow occurs, moisture in the airflow may condense out thereby reducing the moisture content of the airflow re-entering the chamber. In this case, a drain to the exterior of the storage chamber may be provided, to discharge any such condensate for instance into a container. Essentially the same effect may be achieved by including within the air treatment unit a suitable desiccant.

The fan assembly may have a second plenum chamber arranged between the second filter and the external atmosphere with a third filter disposed in relation to that second plenum chamber to filter air entering the second plenum chamber from the external atmosphere. Such a third filter may be secured to the base plate to overlie with clearance the first filter whereby the second plenum chamber is defined by the first and third filters and the base plate.

The third filter may comprise a multi-layer fibrous filter preferably constructed from weather-resistant and waterproof materials. By contrast, the first filter may comprise a porous open-cellular structure of a smaller pore size than that of the third filter.

BRIEF DESCRIPTION OF THE DRAWINGS

By way of example only, certain specific embodiments of this invention will now be described in detail, reference being made to the accompanying drawings, in which.

DETAILED DESCRIPTION OF THE INVENTION

Figure 1:
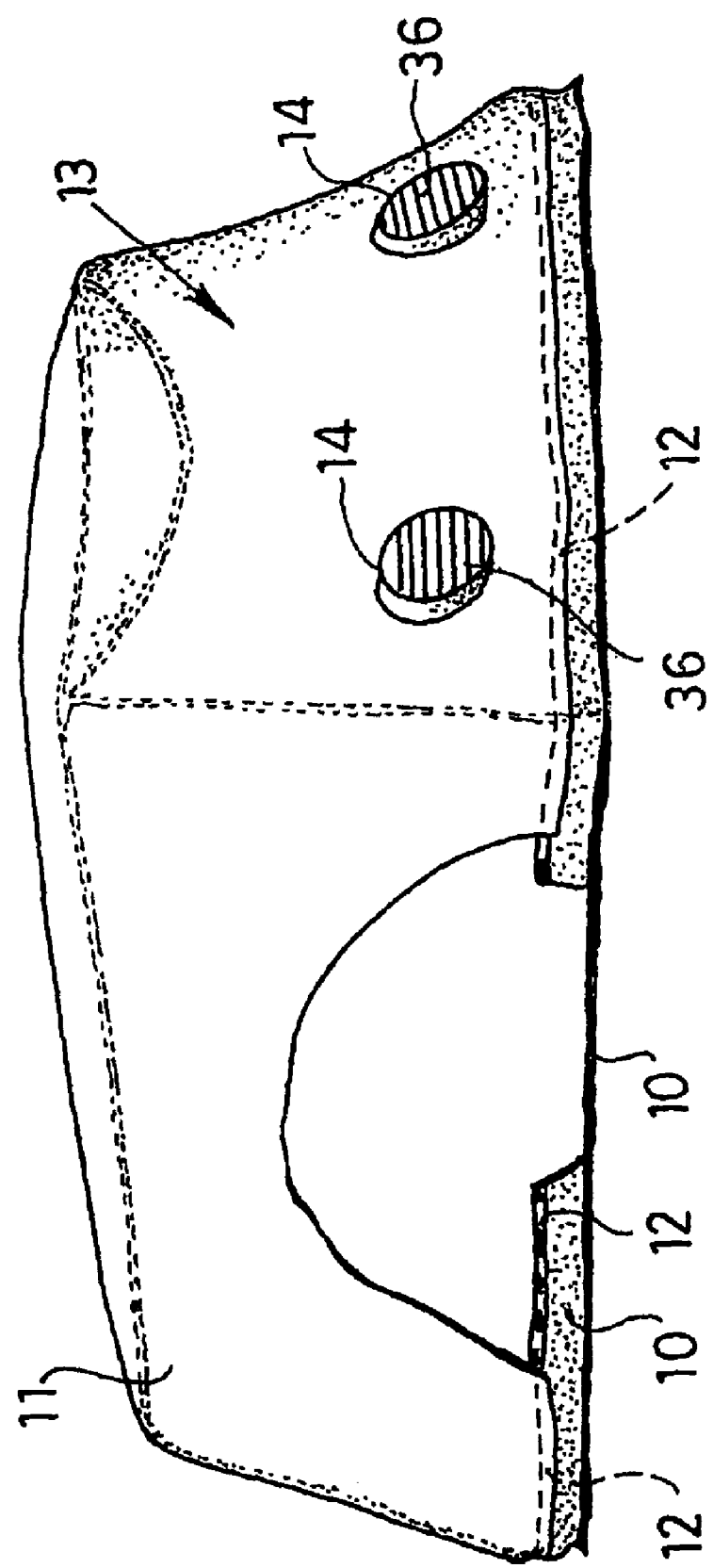
FIG. 1 is a diagrammatic perspective view, partially cut away, of an inflatable storage chamber including a pair of fan assemblies, which chamber is arranged in accordance with this invention.

Referring initially to FIG. 1, there is shown an inflatable storage chamber of a generally known kind. This storage chamber comprises a plastics material base sheet 10 to which is releasably secured a cover sheet 11 preformed to have a generally rectangular shape, when viewed in cross-section both transversely and longitudinally. A two-part fastener 12 has a first part which extends around the lower edge of the cover sheet 11 and a second part which extends around the periphery of the base sheet 10, the two parts of the fastener being connectable together so as to secure the cover sheet 11 to the base sheet 10. For example, the fastener 12 may be a plastic clasp fastener (such as of the kind generally sold under the trade mark Zip) or may be a hook and loop fastener (such as of the kind generally sold under the trade mark Velcro). Whichever form of fastener is employed, the cover sheet 11 should relatively easily be releasable from the base sheet but when the fastener connects the cover sheet to the base sheet, the two sheets should securely be held together.

Two circular holes are formed in an end wall 13 of the cover sheet 11 and in each of those holes is mounted a respective fan assembly 14. Those assemblies 14 are arranged to draw air from the external atmosphere and drive that air into the storage chamber. During an initial period of operation, the fan assemblies will inflate the chamber such that the air pressure within the chamber becomes super-atmospheric, whereafter the pressure within the storage chamber will be maintained. Any air leaking through the fastener 12 will be replaced by fresh air drawn from the external atmosphere. In addition to the leakage through the fastener vents (not shown) may be provided through the cover sheet 11, which vents may be adjusted in order to control the outflow of air from the storage chamber.

Figure 2:
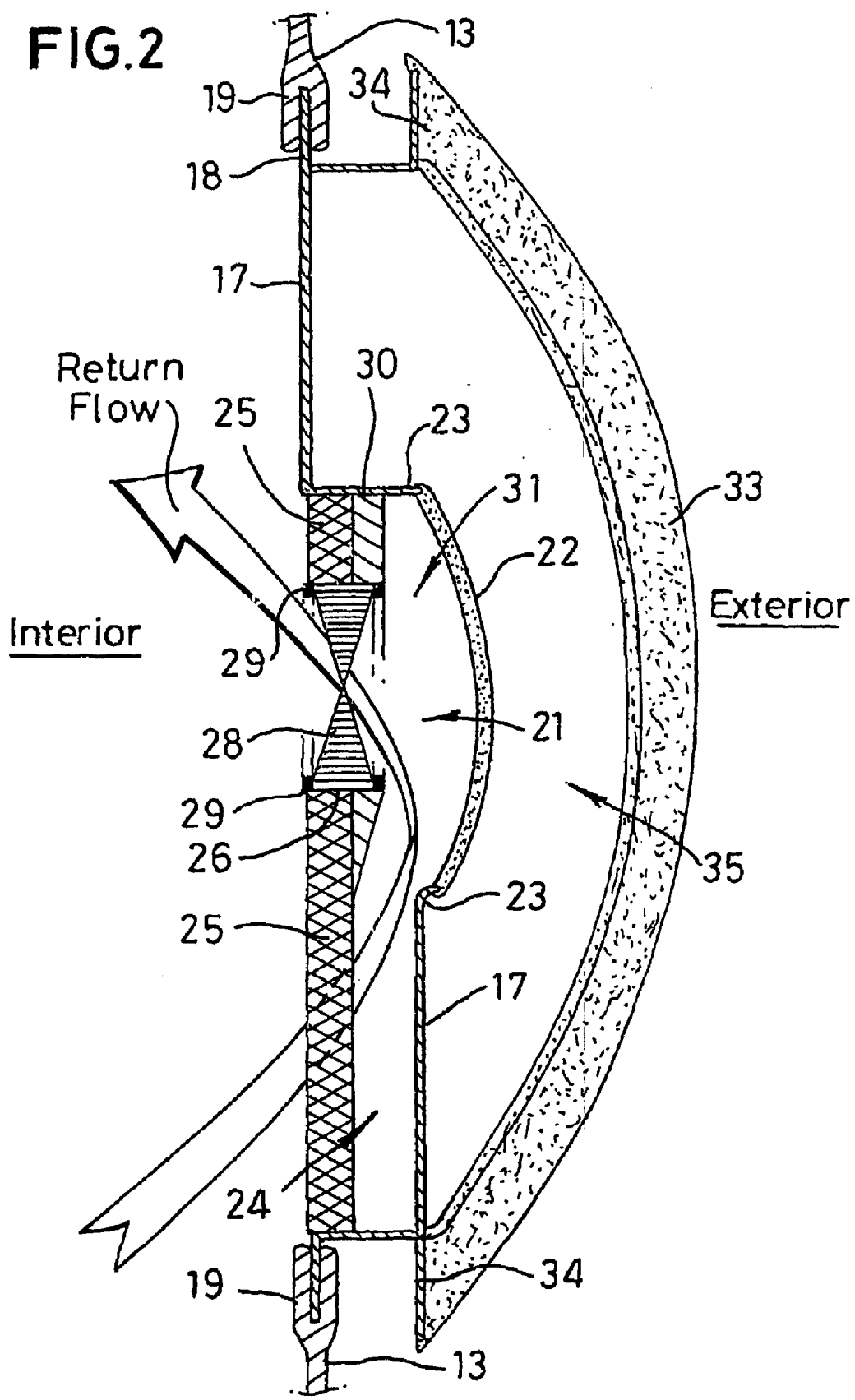
FIG. 2 is a vertical section through a first embodiment of a fan assembly, for use with the storage chamber of FIG. 1.

Referring now to FIG. 2, there is shown a cross-section through one of the fan assemblies 14, mounted in the end wall 13. The fan assembly comprises a base plate 17 including a peripheral flange 18 by means of which the base plate is secured to the hole in the end wall 13 of the storage chamber. For this purpose, the material of the end wall may be reinforced for example with a second, relatively stiff annular piece 19 of plastics material bonded the material of the end wall so as to surround the hole, with the flange 18 sandwiched between the second piece 19 and the material of the end wall itself.

The base plate 17 defines a circular aperture 21 therethrough with a first filter 22 of a porous open cell structure mounted to the edges 23 of that aperture. The base plate also defines a recess 24 in the region of the aperture 21, within which recess is positioned an activated carbon filter 25. An orifice 26 extends through the carbon filter 25 and an electrically driven fan is fitted into that orifice 26. Though shown diagramatically in FIG. 2, the fan comprises an impeller 28 mounted on the shaft of an electric motor (not shown) supported within a frame 29, which frame is positioned within the orifice 26. The motor typically is a low voltage dc motor and the overall fan may be similar to those widely employed in the computer industry, for cooling power supplies and the like. The fan may additionally be supported by means of an insulator 30 connecting the fan frame 29 back to the base plate 17, to relieve loads on the activated carbon filter 25.

In the above manner, a first plenum chamber 31 is defined between the activated carbon filter 25, the base plate 17 and the first filter 22. Upon operation of the fan 27 to drive air into the storage chamber on which the fan assembly is mounted, air may enter the plenum chamber 31 either through the first filter 22 or through the activated carbon filter 25.

A second filter 33 of generally convex form has its periphery supported on lips 34 provided on the base plate 17, so as to extend over the first filter 22 but with clearance thereby to define a second plenum chamber 35. Thus, air passing through the first filter 22 to enter the first plenum chamber 31 must initially pass through the second filter 33 from the external atmosphere, to enter the second plenum chamber 35.

In normal operation, the air driven into the storage chamber will consist of a mixture of air drawn from that storage chamber to be recirculated and also a small quantity of air drawn from outside the storage chamber, to replace losses from the chamber. So long as the storage chamber remains inflated, the first plenum chamber 31 will be at a super-atmospheric pressure by virtue of the returning airflow from within the chamber, In this way the flow of air from outside the storage chamber through the second filter 33 will largely be restricted by the super-atmospheric pressure within the first plenum chamber 31. Only in the event that the leakage out of the storage chamber is such that the pressure will start to fall within the chamber will air flow into the first plenum chamber from the second plenum chamber, to make good the losses.

During initial inflation of the storage chamber, all of the air driven by the fan into the storage chamber will be used to inflate the chamber. Thus, there will be no return flow through the activated carbon filter 25 into the first plenum chamber 31 during this stage of the operation; rather, all of the air driven by the fan into the chamber will be derived from the second plenum chamber 35.

In order to achieve the above functionality it is important that the first filter 22 and the second filter 33 have appropriate characteristics, which may easily be determined empirically. For example the first filter 22 may be of an open cellular form with a relatively small pore size and the second filter 33 may comprise a multi-layer fibrous filter with a greater pore size. The second filter 33 may be of weather resistant materials though as shown in FIG. 1 the fan assembly may be protected by means of a louvre cover 36.

Figure 3:
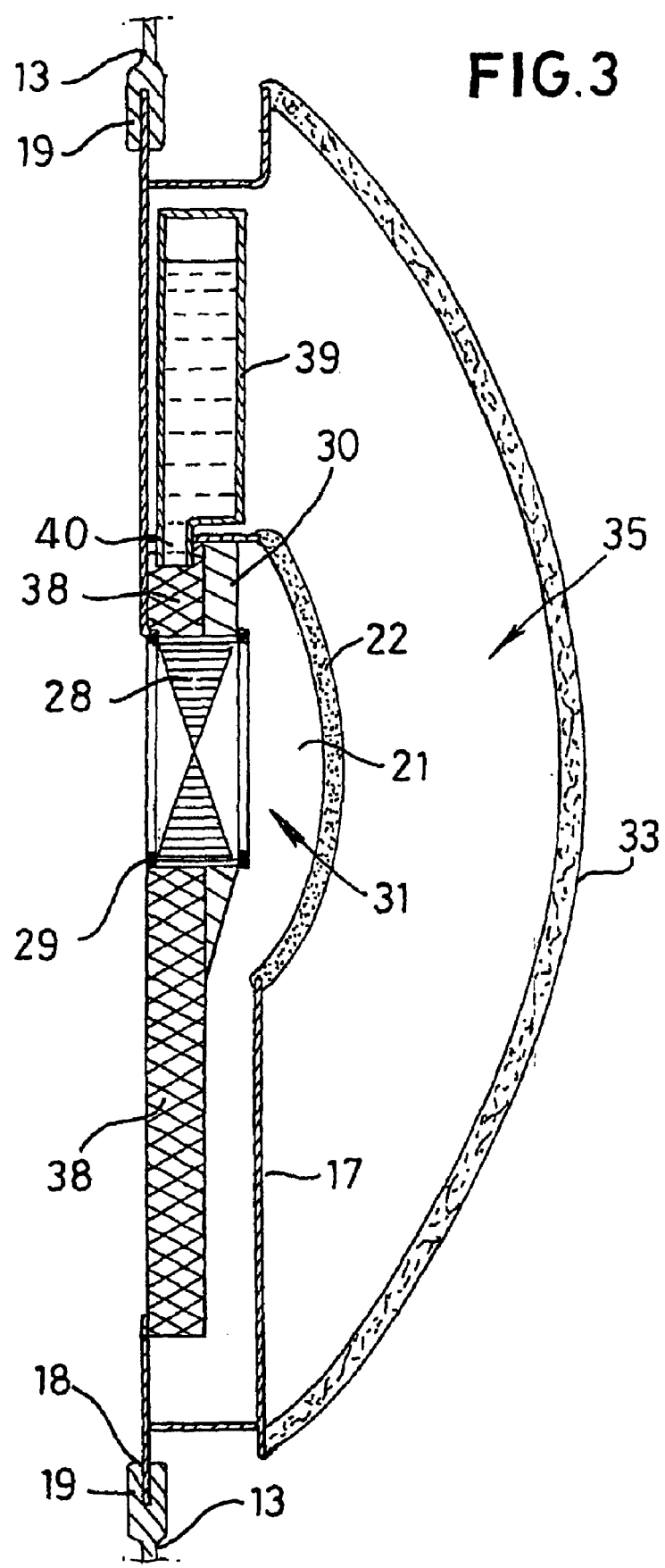
FIGS. 3, 4 and 5 are views similar to that of FIG. 2, but respectively through second, third and fourth embodiments of a fan assembly.

FIG. 3 shows a second embodiment of the fan assembly generally similar to that of FIG. 2 and like parts are given like reference characters; those parts will not be described again here.

In the arrangement of FIG. 3 the activated carbon filter 25 of FIG. 2 is replaced by an open cell polyurethane foam filter 38. A liquid storage vessel 39 is disposed over the filter 38 and has a nozzle 40 having an orifice to control the outflow of liquid from the vessel into the filter 38. In this way, the filter 38 will become impregnated with the liquid from the vessel 39 and the air flow through that filter will thus entrain the liquid, in vapour form. In turn, the air flow entering the chamber will carry the vapour, to treat whatever article might be positioned within the chamber. Typically, the liquid within the vessel 39 is a vapour-phase corrosion inhibitor, but could instead be some other chemical—for example a fumigant or insecticide.

FIG. 3 shows a third fan assembly and again like parts with those of the previous embodiments are given like reference characters and will not be described again here. The fan 27 is carried on a firm but resilient foam mount 41 pressed into a recess in the base plate 42 similar to base plate 17. Base plate 42 also provides a cell 43, a further opening 44 through the base plate communicating with the interior of the cell. Mounted within that cell 43 is a Peltier element 45 having fins 46 whereby operation of the Peltier element will cool air flowing over that element. Provided the cooling is sufficiently great, moisture in the air flow from the storage chamber and passing over the element will condense out to fall into a water trap 47 at the bottom of the cell 43. A drainpipe 48 leads away from the water trap 47 to the exterior of the storage chamber.

Figure 4:
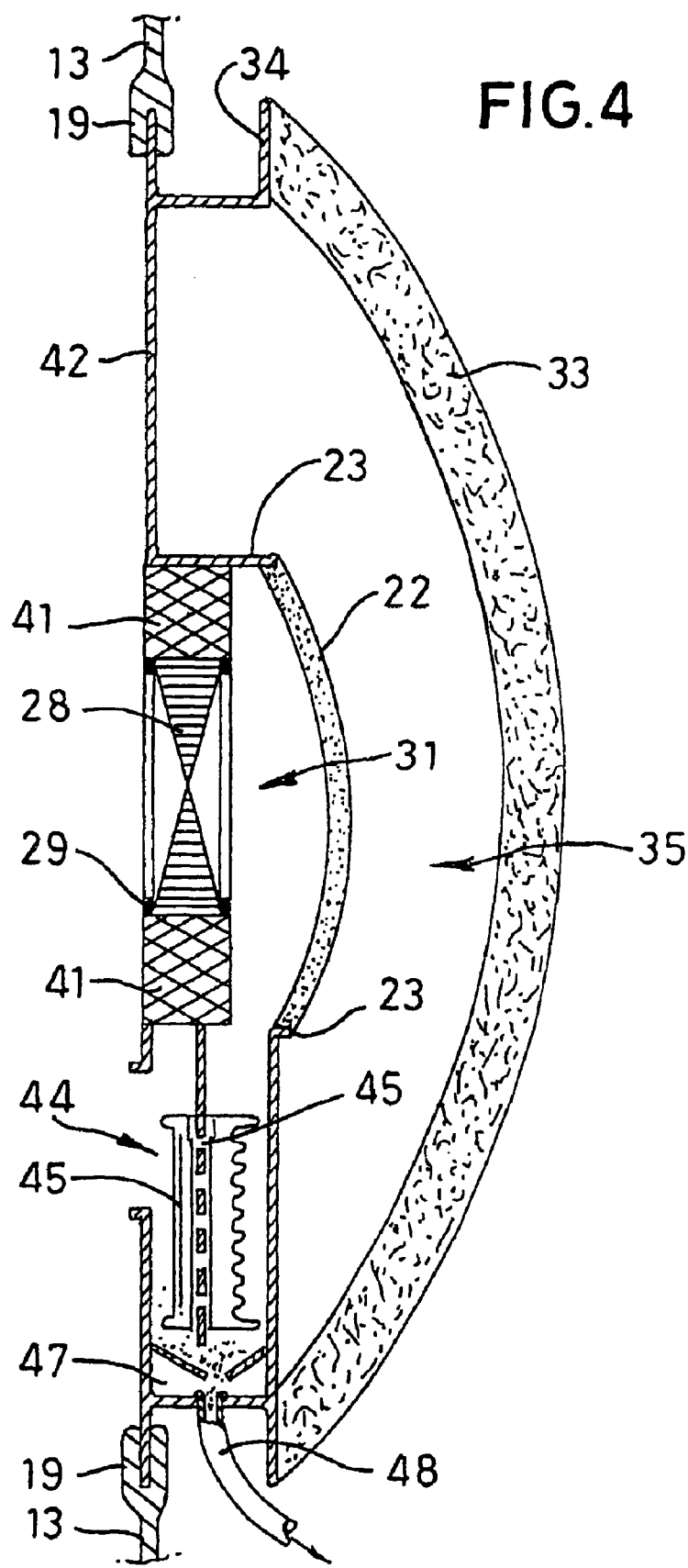

In other respects, the arrangement of FIG. 4 operates substantially as has been described above with reference FIG. 2.

Figure 5:
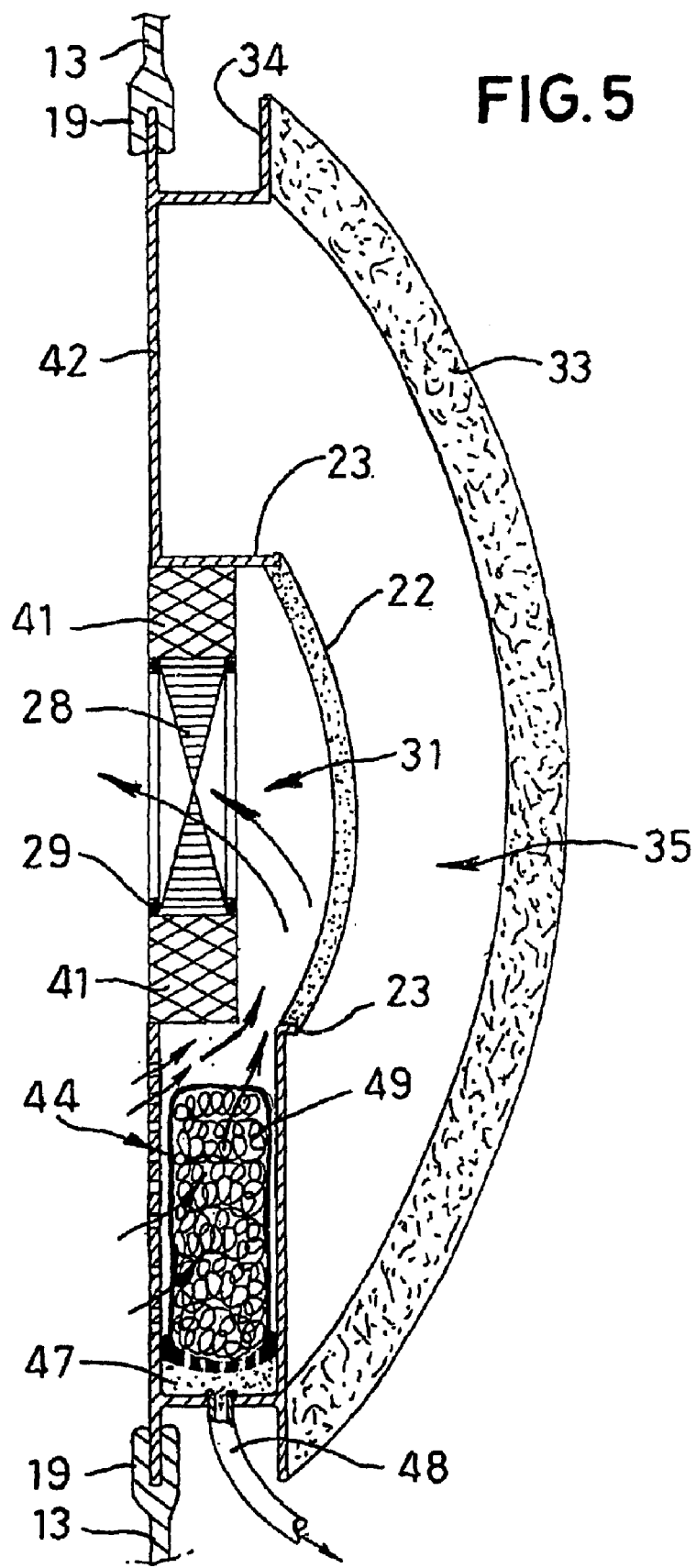

FIG. 5 shows yet another embodiment of fan assembly. This assembly is similar to that of FIG. 4; like parts are given like reference numbers and will not be described again here. In the arrangement of FIG. 5 the Peltier element 45 is replaced by a desiccant 49 provided in a porous bag or provided on a card. The desiccant will draw moisture out of the air flow being recirculated by the fan. As with the previous embodiment, once the desiccant has become saturated the water will fall into a water trap 47 and so to a drain pipe 48 to be led away from the storage chamber.

What is claimed is:

1. A storage chamber comprising an essentially closed space defined by a base sheet, flexible plastics material cover having a periphery which is connected to the base sheet but which cover is at least partially releasable from the base sheet to give access to the space, the cover having an opening therethrough, and a fan assembly including an electrically-driven fan mounted to the opening through the cover to drive air into the essentially closed space to inflate the chamber, characterised in that the fan assembly has a base plate defining an aperture therethrough which base plate is mounted to said cover with said aperture in register with the opening through the cover, and a first plenum chamber is formed on the upstream side of the fan whereby the fan draws air from the first plenum chamber and drives that air through the aperture in the base plate into said space, the fan assembly further including an air treatment unit disposed in or over a further opening through the base plate between said space and the first plenum chamber and a first filter disposed in or over an opening between the first plenum chamber and the external atmosphere, whereby the air driven into said space is a mixture of air drawn from the external atmosphere through the first filter and air drawn from said space through the air treatment unit into the first plenum chamber which latter air is circulated into the space.

2. A storage chamber as claimed in claim 1, wherein the air treatment unit comprises a second filter.

3. A storage chamber as claimed in claim 2, wherein the second filter comprises an activated carbon filter.

4. A storage chamber as claimed in claim 2, wherein the second filter is provided within said aperture in the base plate and the fan is mounted in an opening formed through the filter.

5. A storage chamber as claimed in claim 1, wherein the fan is mounted in an opening through a block of resilient material which resilient material is supported in the aperture through the base plate.

6. A storage chamber as claimed in claim 1, wherein the air treatment unit includes means to entrain a treatment liquid in the air flow from said space to the first plenum chamber.

7. A storage chamber as claimed in claim 6, wherein the treatment liquid comprises a vapour-phase corrosion inhibitor to assist in corrosion-prevention of an article stored in said space.

8. A storage chamber as claimed in claim 1, wherein the air treatment unit includes means to cool the air flow from said space to the first plenum chamber.

9. A storage chamber as claimed in claim 8, wherein the air treatment unit includes a drain for liquid condensed from the air flow, thereby to reduce the moisture content of that air flow.

10. A storage chamber as claimed in claim 1, wherein the air treatment unit includes a desiccant to remove moisture from the air flow from said space to the first plenum chamber.

11. A storage chamber as claimed in claim 1, wherein there is a second plenum chamber arranged between the second filter and the external atmosphere, with a third filter disposed in relation to that second plenum chamber to filter air entering the second plenum chamber from the external atmosphere.

12. A storage chamber as claimed in claim 11, wherein the third filter is secured to the base plate to overlie with clearance the first filter thereby to define in conjunction therewith the second plenum chamber.

13. A storage chamber as claimed in claim 11, wherein the third filter comprises a multi-layer fibrous filter constructed from weather resistant materials.

14. A storage chamber as claimed in claim 1, wherein the first filter comprises a porous filter having an open cellular structure.

* * * * *